United States Patent
Hibino et al.

(10) Patent No.: US 6,852,516 B2
(45) Date of Patent: Feb. 8, 2005

(54) METHOD FOR PRODUCING L-GLUTAMIC ACID BY FERMENTATION

(75) Inventors: Wataru Hibino, Kawasaki (JP); Yasuhiko Yoshihara, Kawasaki (JP); Masakazu Sugimoto, Kawasaki (JP); Harufumi Miwa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/307,320

(22) Filed: Dec. 2, 2002

(65) Prior Publication Data

US 2003/0134397 A1 Jul. 17, 2003

Related U.S. Application Data

(63) Continuation of application No. 09/476,125, filed on Jan. 3, 2000, now abandoned.

(30) Foreign Application Priority Data

Jan. 13, 1999 (JP) ................................. 11-7058

(51) Int. Cl.$^7$ .................... C12P 13/14; C12N 1/20; C12N 15/00; C12N 9/00; C07H 21/04
(52) U.S. Cl. ............ 435/110; 435/41; 435/106; 435/252.3; 435/252.32; 435/320.1; 435/471; 530/350; 536/23.2
(58) Field of Search .................... 435/110, 41, 106, 435/252.3, 252.32, 320.1, 471, 183, 325; 536/23.2; 530/350

(56) References Cited

FOREIGN PATENT DOCUMENTS

WO           99/18228        4/1999

OTHER PUBLICATIONS

Seffernick et al., J. Bacteriol. 183(8):2405–2410, 2001.*

Witkowski et al., Biochemistry 38:11643–11650, 1999.*

Broun et al., Science 282:1315–1317, 1998.

Van de Loo et al., Proc. Natl. Acad. Sci. 92:6743–6747, 1995.

Petra G. Peters–Wendisch et al., Microbiology, vol. 144, pp. 915–927, "Pyruvate Carboxylase from Corynebacterium Glutamicum: Characterization, Expression and Inactivation of the PYC Gene" 1998.

Petra G. Peters–Wendisch, et al., Microbiology, vol. 143, pp. 1095–1103, "Pyruvate Carboxylase as an Anaplerotic Enzyme in Corynebacterium Glutamicum" 1997.

M. A. G. Koffas, et al., Appl. Microbiol Biotechnol, vol. 50, pp. 346–352. "Sequence of the Corynebacterium Glutamicum Pyruvate Carboxylase Gene", 1998.

Bork, Genome Research, 10:348–400, 2000.

* cited by examiner

*Primary Examiner*—Rebecca E. Prouty
*Assistant Examiner*—Delia M. Ramirez
(74) *Attorney, Agent, or Firm*—Oblon, Spivak, McClelland, Maier & Neustadt, P.C.

(57) ABSTRACT

A coryneform bacterium which has enhanced intracellular pyruvate carboxylase activity obtained by increasing copy number of a gene encoding the intracellular pyruvate carboxylase, or by enhancing function of a expression regulatory sequence for the gene, and has L-glutamic acid-producing ability is cultured in a medium so that L-glutamic acid should be produced and accumulated in the culture, and L-glutamic acid is collected from the culture.

14 Claims, 1 Drawing Sheet

METHOD FOR PRODUCING L-GLUTAMIC ACID BY FERMENTATION

This application is a continuation of U.S. application Ser. No. 09/476,125 filed on Jan. 3, 2000, now abandoned.

BACKGROUND OF THE INVENTION

1. Technical Field

The present invention relates to a method for producing L-glutamic acid by fermentation. L-glutamic acid is an important amino acid as food, medicines and so forth.

2. Related Art

L-glutamic acid has conventionally been produced mainly by fermentation utilizing L-glutamic acid-producing coryneform bacteria belonging to the genus *Brevibacterium*, *Corynebacterium*, or *Microbacterium*, or variants thereof (Amino Acid Fermentation, Gakkai Shuppan Center, pp.195–215, 1986).

In recent years, there have been disclosed techniques for breeding L-glutamic acid-producing coryneform bacteria by utilizing genetic recombination techniques. For example, it has been disclosed that an α-ketoglutarate dehydrogenase-deficient L-glutamic acid-producing coryneform bacterium in which the enzyme has been deleted by destroying the gene for the enzyme, for example, can produce and accumulate a marked amount of L-glutamic acid when it is cultured in a medium containing an excessive amount of biotin without addition of any biotin activity inhibiting substance such as surface active agents and penicillin to the medium (WO95/34672).

Under an aerobic condition, L-glutamic acid is biosynthesized from saccharides such as glucose. That is, pyruvate produced in the glycolysis pathway is modified with acetyl-CoA, and enters into the tricarboxylic acid cycle, and L-glutamic acid is biosynthesized from an intermediate of the tricarboxylic acid cycle, α-ketoglutarate, through a reaction catalyzed by glutamate dehydrogenase or glutamine synthetase/glutamate synthase branched off from the tricarboxylic acid cycle at the α-ketoglutarate. Based on these findings, there has been disclosed a method for producing L-glutamic acid utilizing a glutamic acid-producing coryneform bacterium harboring a recombinant DNA that contains a gene encoding glutamate dehydrogenase, isocitrate dehydrogenase, aconitate hydratase, and citrate synthase (Japanese Patent Laid-open No. 63-214189).

While the productivity of L-glutamic acid has been improved by breeding of microorganisms such as those mentioned above and by improvement of production methods therefor, it is still desired to develop techniques for further increasing the productivity of L-glutamic acid of microorganisms in order to respond to further increase of demand of L-glutamic acid in future.

On the other hand, a gene encoding pyruvate carboxylase of *Corynebacterium glutamicum* (pyc gene) has already been cloned, and *Corynebacterium glutamicum* whose pyruvate carboxylase activity is enhanced by expression of the gene, and *Corynebacterium glutamicum* the same gene of which is inactivated have been known (Peters-Wendisch, P. G. et al., *Microbiology*, 144, 915–927 (1998)). However, these microorganisms were created as research materials used for the study of enzymes required for the growth of the microorganisms with glucose, and the relationship between pyruvate carboxylase activity and L-glutamic acid productivity has never been elucidated.

DETAILED DESCRIPTION OF THE INVENTION

The present invention has been accomplished in view of the above technical situation, and its object is to provide an efficient method for producing L-glutamic acid. The inventors of the present invention energetically studied in order to achieve the aforementioned object. As a result, the inventors found that the L-glutamic acid-producing ability of coryneform bacteria could be improved by enhancing the activity of pyruvate carboxylase, which is the enzyme catalyzing the reaction of the anaplerotic pathway branched off from the biosynthetic pathway of L-glutamic acid. Thus, they accomplished the present invention.

That is, the present invention relates to a method for producing L-glutamic acid, comprising the steps of culturing a coryneform bacterium has been modified to increase intracellular pyruvate carboxylase activity and L-glutamic acid-producing ability in a medium to produce and accumulate L-glutamic acid in culture, and collecting L-glutamic acid from the culture.

The present invention also provides a method having the characteristics of the aforementioned method, wherein the pyruvate carboxylase activity is enhanced by increasing copy number of a gene encoding the pyruvate carboxylase in a cell of the bacterium, or enhancing a function of expression regulatory sequence for the gene.

The present invention further provides a method having the characteristics of the aforementioned method, wherein the gene encoding pyruvate carboxylase is derived from a coryneform bacterium.

The present invention still further provides a method having the characteristics of the aforementioned method, wherein the medium contains a saccharide and ethanol.

Hereafter, the present invention will be explained in detail.

The method of the present invention utilizes a coryneform bacterium having enhanced intracellular pyruvate carboxylase activity, and L-glutamic acid-producing ability.

The coryneform bacteria in the present invention includes bacteria having been hitherto classified into the genus *Brevibacterium* but united into the genus *Corynebacterium* at present (Int. J. Syst. Bacteriol., 41, 255 (1981)), and include bacteria belonging to the genus *Brevibacterium* closely relative to the genus *Corynebacterium*. Examples of such coryneform L-glutamic acid-producing bacteria include the followings.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagenes* (*Corynebacterium ammoniagenes*)
*Brevibacterium album*

*Brevibacterium cerinum*

*Microbacterium ammoniaphilum*

Specifically, the following strains of these bacteria are exemplified:

*Corynebacterium acetoacidophilum* ATCC13870

*Corynebacterium acetoglutamicum* ATCC15806

*Corynebacterium alkanolyticum* ATCC21511

*Corynebacterium callunae* ATCC15991

*Corynebacterium glutamicum* ATCC13020, 13032, 13060

*Corynebacterium lilium* (*Corynebacterium glutamicum*) ATCC15990

*Corynebacterium melassecola* ATCC17965

*Corynebacterium thermoaminogenes* AJ12340 FERM BP-1539)

*Corynebacterium herculis* ATCC13868

*Brevibacterium divaricatum* (*Corynebacterium glutamicum*) ATCC14020

*Brevibacterium flavum* (*Corynebacterium glutamicum*) ATCC13826, ATCC14067

*Brevibacterium immariophilum* ATCC14068

*Brevibacterium lactofermentum* (*Corynebacterium glutamicum*) ATCC13665, ATCC13869

*Brevibacterium roseum* ATCC13825

*Brevibacterium saccharolyticum* ATCC14066

*Brevibacterium thiogenitalis* ATCC19240

*Corynebacterium ammoniagenes* (*Brevibacterium ammoniagenes*) ATCC6871

*Brevibacterium album* ATCC15111

*Brevibacterium cerinum* ATCC15112

*Microbacterium ammoniaphilum* ATCC15354

In order to amplify the pyruvate carboxylase activity in a coryneform bacterial cell, a recombinant DNA can be prepared by ligating a gene fragment encoding pyruvate carboxylase with a vector functioning in the bacterium, preferably a multi-copy vector, and introduced into the host coryneform bacterial cell having L-glutamic acid producing ability to transform the cell. The copy number of the gene encoding pyruvate carboxylase (referred to as the "pyc gene" hereinafter) in the cell of the transformant is thereby increased, and as a result, the pyruvate carboxylase activity is amplified.

As the pyc gene, those derived form coryneform bacteria as well as those derived from other organisms such as bacteria belonging to the genus *Escherichia* may be used. The nucleotide sequence of the pyc gene of a coryneform bacterium has already been reported (Peters-Wendisch, P. G. et al., *Microbiology*, 144, 915–927 (1998)). Therefore, the pyc gene can be obtained by PCR (polymerase chain reaction; see White, T. J. et al; *Trends Genet*. 5, 185 (1989)) utilizing primers prepared based on the nucleotide sequence and chromosomal DNA of microorganism such as *Brevibacterium lactofermentum* as a template. Examples of the primers include the primers represented in Sequence Listing as SEQ ID NOS: 1 and 2.

The plasmid used for the cloning of the pyc gene may be any plasmid which is replicable in a microorganism such as a bacterium belonging to the genus *Escherichia*, and specific examples thereof include pBR322, pTWV228, pMW119, pUC19 and so forth.

The plasmids which function in coryneform bacteria means plasmids autonomously replicable in coryneform bacteria. The plasmids include, for example, the followings.

pAM330 (see Japanese Patent Laid-open No. 58-67699)

pHM1519 (see Japanese Patent Laid-open No. 58-77895)

pAJ655 (see Japanese Patent Laid-open No. 58-192900)

pAJ611 (see the same)

pAJ1844 (see the same)

pCG1 (see Japanese Patent Laid-open No. 57-134500)

pCG2 (see Japanese Patent Laid-open No. 58-35197)

pCG4 (see Japanese Patent Laid-open No. 57-183799)

pCG11 (see the same)

pHK4 (see Japanese Patent Laid-open No. 5-7491)

In order to prepare recombinant DNA by ligating the pyc gene encoding pyruvate carboxylase and a vector which can function in a cell of coryneform bacterium, the vector is digested by restriction enzyme(s) corresponding to the termini of the pyc gene. Ligation is generally performed by using a ligase such as T4 DNA ligase.

To introduce the recombinant DNA prepared as described above to a coryneform bacterium, any known transformation methods can be employed. For instance, employable are a method of treating recipient cells with calcium chloride so as to increase the permeability of DNA, which has been reported for *Escherichia coli* K-12 [see Mandel, M. and Higa, A., J. Mol. Biol., 53, 159 (1970)]; and a method of preparing competent cells from cells which are at the growth phase followed by introducing the DNA thereinto, which has been reported for *Bacillus subtilis* [see Duncan, C. H., Wilson, G. A. and Young, F. E., Gene, 1, 153 (1977)]. In addition to these, also employable is a method of making DNA-recipient cells into the protoplast or spheroplast which can easily take up recombinant DNAs followed by introducing the recombinant DNA into the cells, which is known to be applicable to *Bacillus subtilis*, actinomycetes and yeasts [see Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)]. The method of transformation used in embodiments of the present invention is the electric pulse method (refer to Japanese Patent Publication Laid-Open No. 2-207791).

Enhancement of pyruvate carboxylase activity can also be achieved by introducing multiple copies of the pyc gene into the chromosomal DNA of coryneform bacterium. In order to introduce multiple copies of the pyc gene in the chromosomal DNA of coryneform bacterium, the homologous recombination is carried out using a sequence whose multiple copies exist in the chromosomal DNA as targets. As sequences whose multiple copies exist in the chromosomal DNA, repetitive DNA, inverted repeats exist at the end of a transposable element can be used. Also, as disclosed in Japanese Patent Laid-open No. 2-109985, it is possible to incorporate the pyc gene into transposon, and allow it to be transferred to introduce multiple copies of the pyc gene into the chromosomal DNA. By either method, the number of copies of the pyc gene within cells of the transformant strain increases, and as a result, pyruvate carboxylase activity is enhanced. Enhancement of an expression regulatory sequence may be combined with increasing the copy number of the pyc gene.

The enhancement of pyruvate carboxylase activity can also be obtained by, besides being based on the aforementioned gene enhancement, enhancing an expression regulatory sequence for the pyc gene. Specifically, it can be attained by replacing an expression regulatory sequence of pyc gene on chromosome DNA or plasmid, such as a promoter, with a stronger one (see Japanese Patent Laid-open No. 1-215280). For example, lac promoter, trc promoter, tac promoter, PR promoter and PL promoter of lambda phage and the like are known as strong promoters. Substitution of these promoters enhances expression of the pyc gene, and hence the pyruvate carboxylase activity is enhanced.

In the coryneform bacteria of the present invention, the activity of an enzyme which catalyzes the biosynthesis of L-glutamic acid other than pyruvate carboxylase may be enhancing. Illustrative examples of the enzyme for catalyzing the biosynthesis of L-glutamic acid include glutamate dehydrogenase, glutamine synthetase, glutamate synthase, isocitrate dehydrogenase, aconitate hydratase, citrate synthase, phosphoenolpyruvate carboxylase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase and the like.

The activity of an enzyme which catalyzes a reaction for generating a compound other than L-glutamic acid by branching off from the biosynthetic pathway of L-glutamic acid may be decreased or lost. Illustrative examples of the enzyme which catalyzes a reaction for generating a compound other than L-glutamic acid by branching off from the biosynthetic pathway of L-glutamic acid include a-ketoglutarate dehydrogenase, isocitrate lyase, phosphate acetyltransferase, acetate kinase, acetohydroximate synthase, acetolactate synthase, formate acetyltransferase, lactate dehydrogenase, glutamate decarboxylase, 1-pyrroline dehydrogenase and the like.

Furthermore, by introducing a thermosensitive mutation for a biotin activity inhibiting substance such as surface active agents into a coryneform bacterium having L-glutamic acid-producing ability, the bacterium becomes to be able to produce L-glutamic acid in a medium containing an excessive amount of biotin in the absence of a biotin activity inhibiting substance (see WO96/06180). As such a coryneform bacterium, the *Brevibacterium lactofermentum* AJ13029 strain disclosed in WO96/06180 can be mentioned. The AJ13029 strain was deposited at the National Institute of Bioscience and Human-Technology, Agency of Industrial Science and Technology on Sep. 2, 1994, and received an accession number of FERM P-14501. Then, its was transferred to an international deposition under the provisions of the Budapest Treaty on Aug. 1, 1995, and received an accession number of FERM BP-5189.

Methods for construction of genomic DNA library, hybridization, PCR, preparation of plasmid DNA, digestion and ligation of DNA, transformation and the like are described in Sambrook, J., Fritsch, and E. F., Maniatis, T., "Molecular Cloning A Laboratory Manual, Second Edition", Cold Spring Harbor Laboratory Press (1989).

L-glutamic acid can efficiently be produced by culturing a coryneform bacterium of which pyruvate carboxylase activity has been enhanced as described above in a medium to produce and accumlate L-glutamic acid in the medium, and collecting L-glutamic acid from the medium.

The medium to be used is not particularly limited, and any conventional media containing a carbon source, nitrogen source, inorganic ions, and other organic trace nutrients as required may be used.

As the carbon source, it is possible to use sugars such as glucose, lactose, galactose, fructose, starch hydrolysate and molasses or the like; alcohols such as ethanol, inositol; or organic acids such as acetic acid, fumaric acid, citric acid and succinic acid or the like.

By using the aforementioned saccharides, preferably glucose, together with ethanol as the carbon source, the L-glutamic acid production amount can be increased. The amount of ethanol in the carbon source is preferably 5% or more, more preferably 10–75%, particularly preferably 20–30%.

As the nitrogen source, it is possible to use inorganic ammonium salts such as ammonium sulfate, ammonium chloride or ammonium phosphate; organic nitrogen such as soybean hydrolysate; ammonia gas; or aqueous ammonia.

As the inorganic ions (or sources thereof), added is a small amount of potassium phosphate, magnesium sulfate, iron ions, manganese ions and so forth. As for the organic trace nutrients, it is desirable to add required substances such as vitamin $B_1$, yeast extract and so forth in a suitable amount as required.

Cultivation is preferably carried out under an aerobic condition for 16–72 hours. The cultivation temperature is controlled at 20° C. to 45° C., and pH is controlled at 5–8.5 during cultivation. Inorganic or organic, acidic or alkaline substances as well as ammonia gas or the like can be used for pH adjustment.

Collection of L-glutamic acid from a fermented liquor is usually carried out by combining an ion exchange resin method, a precipitation method and other known methods.

According to the present invention, there is provided an efficient method for producing L-glutamic acid utilizing a coryneform bacterium. The present invention can also be utilized for breeding of L-glutamic acid-producing coryneform bacteria.

BEST MODE FOR CARRYING OUT THE INVENTION

Figure 1:
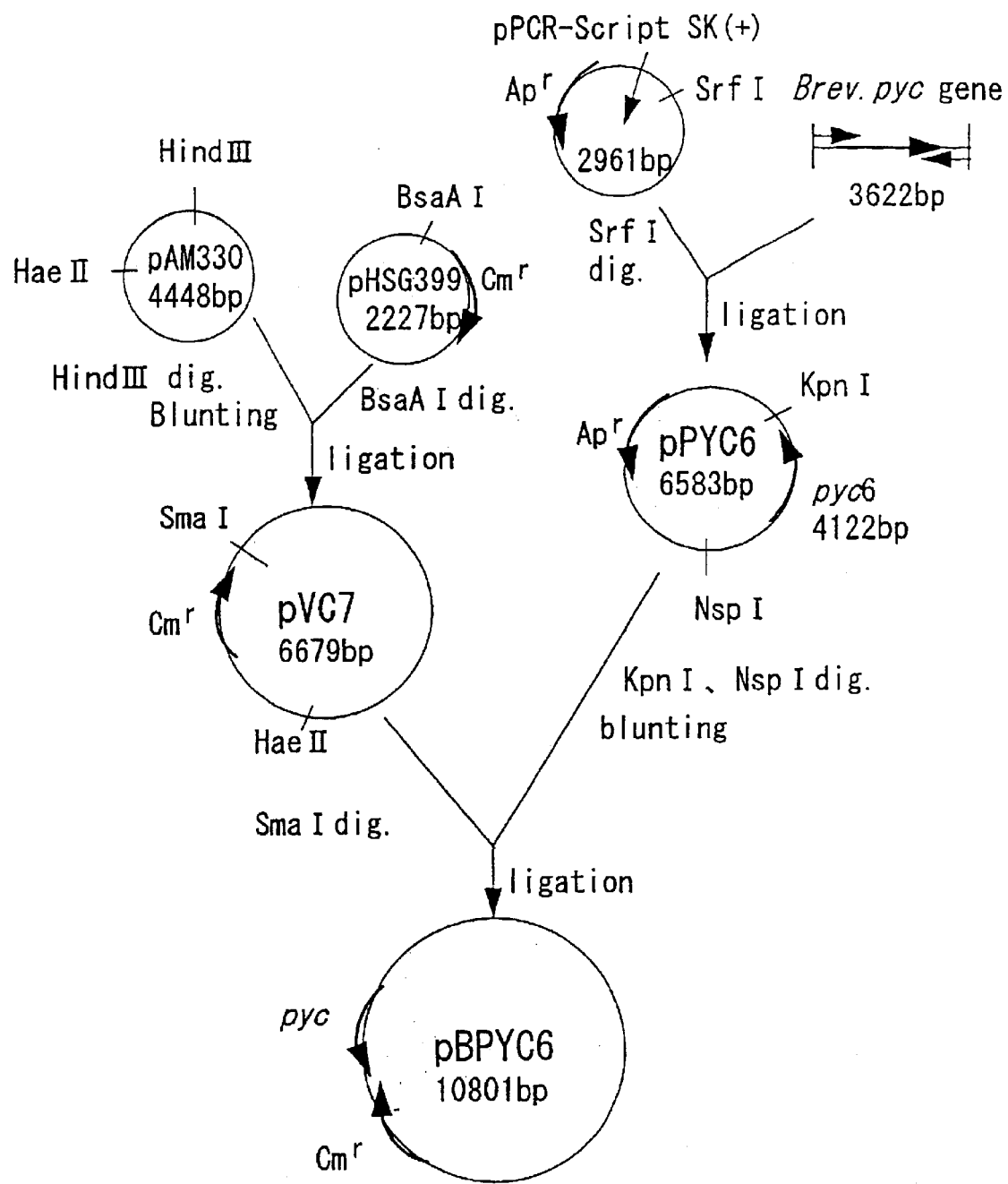
FIG. 1 shows construction of plasmid pBPYC6 that contains a cloning vector for coryneform bacteria, pVC7, and the pyruvic acid carboxylase gene (pyc) introduced into the plasmid pVC7.

The present invention will be further specifically explained hereinafter with reference to the following examples.

EXAMPLE 1

<1> Production of the *Brevibacterium lactofermentum* with Enhanced Pyruvate Carboxylase Activity The pyc gene of *Brevibacterium lactofermentum* ATCC13869 was amplified by PCR (Polymerase Chain Reaction; see White, T. J. et al., *Trends Genet.* (1990) 224, 317–324). Oligonucleotide primers having the nucleotide sequences shown as SEQ ID NO: 1 and 2 were synthesized based on the known nucleotide sequence of a pyc gene derived from *Corynebacterium glutamicum* (Peters-Wendisch, P. G. et al., *Microbiology*, 144, 915–927 (1998)), and PCR was performed by using the primers and *Brevibacterium lactofermentum* ATCC13869 chromosomal DNA as a template. The PCR was performed with a cycle consisting of 94° C. for 30 seconds, 55° C. for 1 second, and 72° C. for 2.5 minutes repeated for 25 cycles by using ExTaqDNA polymerase (produced by Takara Shuzo Co., Ltd.) on DNA Thermal Cycler MP produced by Takara Shuzo Co., Ltd.

Then, the gene fragment amplified by PCR (3622 bp) was subjected to agarose electrophoresis, cut out from the gel, and purified in a conventional manner. The fragment was inserted into SrfI site of plasmid pPCR-Script SK(+) by using pCR-Script Amp kit (Stratagene) and according to the method specified in the manufacturer's instruction, and the host attached to the kit was transformed with the obtained recombinant plasmid to obtain a plasmid pPYC6 (FIG. 1).

The cloned sequence was determined for its DNA sequence by the method of Sanger et al. (F. Sanger et al., *Proc. Natl. Acad. Sci.*, 74, 5463 (1977) etc.), and it was confirmed to be the target sequence.

A newly constructed cloning vector for coryneform bacteria, pVC7, was used as the vector for introducing the pyc gene into coryneform bacteria. pVC7 was constructed by ligating a cryptic plasmid of *Brevibacterium lactofermentum*, pAM330, to a vector for *Escherichia Coli*, pHSG399 (chloramphenicol resistant, see Takeshita, S. et al., *Gene*, 61, 63–74 (1987)) as follows (FIG. 1). pAM330 was prepared from *Brevibacterium lactofermentum* ATCC13869. pHSG399 was digested with an enzyme cleaving one site, BsaAI (produced by New England Biolabs), then digested with HindIII (produced by Takara Shuzo Co., Ltd.), and ligated to pAM330 blunt-ended with T4 DNA polymerase. The two kinds of plasmids produced depending on the insertion direction of pAM330 into pHSG399 were designated as pVC6 and pVC7. Among these two kinds of plasmids, one generating 1.7 kb and 5.0 kb fragments is pVC6, and one generating 2.8 kb and 3.9 KB fragments is pVC7, when they are digested with HaeII (produced by Takara Shuzo Co., Ltd.). pVC6 and pVC7 are autonomously replicable in cells of *Escherichia coli* and *Brevibacterium lactofermentum*, and they contain a multi-cloning site derived from pHSG399, and lacZ'.

The plasmid pPYC6 which was incorporated with the pyc gene was digested with KpnI (produced by Takara Shuzo Co., Ltd.), and NspI (produced by Takara Shuzo Co., Ltd.) to excise the pyc gene fragment, which was then blunt-ended. The blunt-ending was performed by using DNA Blunting kit (produced by Takara Shuzo Co., Ltd.). The blunt-ended DNA fragment was inserted into SmaI site of pVC7 to construct pBPYC6 (FIG. 1). Then, *Brevibacterium lactofermentum* ATCC13869 was transformed with pBPYC6. As a control, *Brevibacterium lactofermentum* ATCC13869 was transformed with pVC7. The transformation was performed by the electric pulse method (see Japanese Patent Laid-open No. 2-207791).

<2> Evaluation of L-glutamic Acid Productivity

The obtained *Brevibacterium lactofermentum* ATCC13869/pBPYC6 and *Brevibacterium lactofermentum* ATCC13869/pVC7 were investigated for the productivity of L-glutamic acid. The medium used had a composition of 1.5 g/dl of glucose, 0.1 g/dl of potassium dihydrogenphosphate, 0.1 g/dl of magnesium sulfate heptahydrate, 0.001 g/dl of iron sulfate heptahydrate, 0.001 g/dl of manganese sulfate tetrahydrate or pentahydrates, 300 μg/l of biotin, 48 mg/dl (as total nitrogen amount) of soybean hydrolysate, 2.0 g/dl of ammonium sulfate, 0.01 ml/dl of anti-foaming agent (GD-113), 0.3 g/dl of ethanol, 0.2 g/dl of polyoxyethylenesorbitan monopalmitate, 5.0 g/dl of calcium carbonate, and 5 μg/ml of chloramphenicol. The cultivation was performed by using Sakaguchi flasks.

The pre-culture was performed at 31.5° C. for 7 hours in a medium that had the same composition as mentioned above except that it did not contain polyoxyethylenesorbitan monopalmitate. The main culture was performed at 31.5° C. for 16 hours. The results of evaluation of the cultivation are shown in Table 1. The amino acid composition of the starting medium was calculated from the content of the soy bean hydrolysate.

In the strain in which pyc gene had been amplified, the accumulation of glutamic acid was improved by 3.8%, and the yield based on the saccharide was improved by 2.1% as compared with the control.

TABLE 1

| Medium | Glutamic acid [mg/dl] | Yield [%] | Aspartic acid [mg/dl] | Alanine [mg/dl] |
|---|---|---|---|---|
| Starting medium | 60 | — | 36.0 | 18.5 |
| ATCC13869/pVC7 | 1012 | 52.9 | 5.16 | 4.68 |
| ATCC13869/pBPYC6 | 1050 | 55.0 | 10.31 | 4.19 |

EXAMPLE 2

*Brevibacterium lactofermentum* ATCC13869/pBPYC6 and *Brevibacterium lactofermentum* ATCC13869/pVC7 were cultured in the same manner as in Example 1 <2> except that glucose and ethanol were added to the medium in a ratio shown in Table 2 (2 g/dl in total). After the cultivation, the amount of L-glutamic acid accumulated in the medium was measured. The results are shown in Table 2.

By using ethanol as the carbon source, the L-glutamic acid production amount is increased. The increase of intracellular pyruvate carboxylase activity has larger effect on the L-glutamic acid production when the ratio of ethanol in the carbon source is 5% or more, preferably 10–75% and most preferably 20–30%.

TABLE 2

| | Yield of L-glutamic acid | | | | |
|---|---|---|---|---|---|
| | Ratio of ethanol in carbon source | | | | |
| Medium | 5% | 10% | 25% | 75% | 100% |
| ATCC13869/pVC7 | 51.8% | 54.3% | 55.5% | 48.0% | 45.1% |
| ATCC13869/pBPYC6 | 52.0% | 59.3% | 72.5% | 59.3% | 54.1% |

What is claimed is:

1. A method for producing L-glutamic acid, comprising:
culturing a coryneform bacterium in a medium containing a saccharide and ethanol under conditions suitable for producing and accumulating L-glutamic acid in culture, wherein said bacterium has been modified to increase the copy number of a gene coding for pyruvate carboxylase so that the intracellular pyruvate carboxylase activity is enhanced, or the promoter of the gene is replaced with a promoter capable of enhancing expression of the gene, whereby the intracellular pyruvate carboxylase activity is enhanced, and
collecting L-glutamic acid from the culture, wherein the concentration of ethanol in the carbon source of said medium is at least 10%,
wherein the gene coding for pyruvate carboxylase is derived from a coryneform bacterium.

2. The method of claim 1, wherein said bacterium has been modified to increase the copy number of a gene coding for pyruvate carboxylase so that the intracellular pyruvate carboxylase activity is enhanced.

3. The method of claim 1, wherein the promoter of the gene is replaced with a promoter capable of enhancing expression of the gene, whereby the intracellular pyruvate carboxylase activity is enhanced.

4. The method of claim 3, wherein said promoter is selected from the group consisting of lac promoter, trc promoter, tac PR promoter of lambda phage, and PL promoter of lambda phage.

5. The method of claim 1, wherein said coryneform bacterium is *Corynebacterium glutamicum*.

6. The method of claim 1, wherein said saccharide is at least one saccharide selected from the group consisting of glucose, lactose, galactose, fructose, starch hydrolysate, and molasses.

7. The method of claim 1, wherein said medium further comprises at least one additive selected from the group consisting of inositol, acetic acid, fumaric acid, citric acid, succinic acid, inorganic ammonium salt, organic nitrogen, ammonia gas, aqueous ammonia, potassium phosphate, magnesium sulfate, iron ion, manganese ion, vitamin $B_1$, and yeast extract.

8. The method of claim 1, wherein said culturing is under aerobic conditions.

9. The method of claim 1, wherein said culturing is for a time ranging from 16 to 72 hours.

10. The method of claim 1, wherein said culturing is at a temperature of 20° C. to 45° C.

11. The method of claim 1, wherein said culturing is at a pH of 5–8.5.

12. The method of claim 1, wherein the concentration of ethanol in the carbon source of said medium ranges from 10% to 75%.

13. The method of claim 1, wherein the concentration of ethanol in the carbon source of said medium ranges from 25% to 75%.

14. The method of claim 1, wherein the concentration of ethanol in the carbon source of said medium ranges from 20% to 30%.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:

-continued

```
<223> OTHER INFORMATION: synthetic DNA

<400> SEQUENCE: 1
tggggcgggg ttagatcctg gggg                                    24

<210> SEQ ID NO 2
<211> LENGTH: 24
<212> TYPE: DNA
<213> ORGANISM: Artificial Sequence
<220> FEATURE:
<223> OTHER INFORMATION: synthetic DNA

<400> SEQUENCE: 2
ctttttacag aaaggtttag gaaa                                    24
```